(12) United States Patent
Ban et al.

(10) Patent No.: US 8,962,302 B2
(45) Date of Patent: Feb. 24, 2015

(54) BIOLOGICAL TISSUE PROCESSING SUBSTRATE FOR FIXING PROTEINS OR PROTEIN DEGRADATION PRODUCTS IN TISSUE FOR ANALYSIS

(75) Inventors: Kazuhiro Ban, Tokyo (JP); Miki Ogawa, Machida (JP); Norihiko Utsunomiya, Machida (JP); Hiroyuki Hashimoto, Yokohama (JP); Manabu Komatsu, Kawasaki (JP); Yohei Murayama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1517 days.

(21) Appl. No.: 11/592,313

(22) Filed: Nov. 3, 2006

(65) Prior Publication Data

US 2007/0105087 A1    May 10, 2007

(30) Foreign Application Priority Data

Nov. 7, 2005   (JP) .................. 2005-322311

(51) Int. Cl.
| | | |
|---|---|---|
| *C12M 1/00* | (2006.01) | |
| *C12M 1/34* | (2006.01) | |
| *C12Q 1/00* | (2006.01) | |
| *C12Q 1/34* | (2006.01) | |
| *C12Q 1/37* | (2006.01) | |
| *C12Q 1/02* | (2006.01) | |
| *C12N 11/14* | (2006.01) | |
| *C12N 11/02* | (2006.01) | |
| *C12N 11/04* | (2006.01) | |
| *G01N 33/68* | (2006.01) | |
| *G01N 33/50* | (2006.01) | |

(52) U.S. Cl.
CPC ........ *G01N 33/6848* (2013.01); *G01N 33/5082* (2013.01)

USPC ........ 435/284.1; 435/287.1; 435/18; 435/23; 435/29; 435/177; 435/182

(58) Field of Classification Search
CPC .......... C12M 1/00; C12M 1/34; C12M 1/343; C12Q 1/00; C12Q 1/34; C12Q 1/37; C12Q 1/02; C12N 11/14; C12N 11/02; C12N 11/04
See application file for complete search history.

(56) References Cited

U.S. PATENT DOCUMENTS

| | | | | |
|---|---|---|---|---|
| 4,141,857 | A * | 2/1979 | Levy et al. | 502/439 |
| 4,605,594 | A * | 8/1986 | Owens et al. | 428/373 |
| 5,395,807 | A * | 3/1995 | Divakar et al. | 501/88 |
| 6,498,039 | B2 * | 12/2002 | Nelson | 436/86 |
| 6,969,614 | B1 | 11/2005 | Liotta et al. | 436/177 |
| 2004/0132080 | A1 | 7/2004 | Kawaguchi et al. | 435/6 |
| 2005/0287681 | A1 | 12/2005 | Nishiuma et al. | 436/524 |
| 2006/0011552 | A1 | 1/2006 | Utsunomiya | 210/695 |
| 2006/0183235 | A1 | 8/2006 | Hashimoto et al. | 436/86 |

FOREIGN PATENT DOCUMENTS

| | | |
|---|---|---|
| JP | 2002-537561 | 11/2002 |
| WO | 2005/003715 | 1/2005 |

* cited by examiner

*Primary Examiner* — David M Naff
(74) *Attorney, Agent, or Firm* — Fitzpatrick, Cella, Harper and Scinto

(57) ABSTRACT

A biological tissue processing substrate for fixing proteins in a biological tissue or degradation products of the proteins, the substrate comprising: a porous body that forms a contact surface with the biological tissue, the porous body holding in pores an enzyme for obtaining the proteins or the degradation products of the proteins from the biological tissue, wherein the proteins or the degradation products obtained by the action of the enzyme are brought into contact with a member consisting of a metal.

3 Claims, 9 Drawing Sheets

BIOLOGICAL TISSUE PROCESSING SUBSTRATE FOR FIXING PROTEINS OR PROTEIN DEGRADATION PRODUCTS IN TISSUE FOR ANALYSIS

BACKGROUND OF THE INVENTION

1. Field of the Invention

The present invention relates to a biological tissue processing substrate, a processing apparatus, a processing method and a processing kit. More particularly, the present invention relates to a biological tissue processing substrate for fixing proteins or degradation products of proteins in biological tissues as a preprocessing for analyzing biological tissues.

2. Description of the Related Art

Recently importance of analysis of protein, a gene product existing in the body, has received attention through progress of genome analysis. Among others, the importance of protein analysis on tissue slice has been noted. For example, many attempts to elucidate proteins involved in recurrence or metastasis from cancer tissue slice have been made. As for well known examples in these analytical means, following means are known.

These are (1) extraction of proteins from biological tissues and cells; (2) separation of proteins; (3) analysis of proteins or degradation products of proteins; and (4) identification of the thus obtained analytical results.

Japanese Patent Application Laid-Open No. 2002-537561 discloses, as a means for extraction of proteins in biological tissues, a method comprising extracting cell population from biological tissues by using laser and solubilizing the proteins contained in the cell population into a solution containing surface active agents, etc. The solubilized proteins by such method is isolated and analyzed by mass spectrometry, etc.

Further, information acquisition method and information acquisition apparatus based on TOF-SIMS (time of flight secondary ion mass spectrometry) for the purpose of visualizing two-dimensional distribution of protein on the biological tissue slice have been disclosed in the pamphlet of International Publication No. WO2005/003715A2. This method discloses such that ionization promoting substance and/or digestive enzyme are directly supplied to the biological tissue slice by using ink-jet method. Information relating to a type of proteins (including information on specific degradation of peptide by digestive enzyme) is visualized with maintaining the location information thereof by TOF-SIMS.

In Japanese Patent Application Laid-Open No. 2002-537561, since the protein is extracted from the population of cells, the method disclosed in the publication is not suited to specify individually from what cells the detected protein is derived. Further, according to the description disclosed in International Publication No. WO 2005/003715 A2, information on protein distribution in some biological tissues can be obtained. However, in case of obtaining two-dimensional distribution information with good accuracy by using such method, the solution for digestive enzyme treatment should be supplied individually to micro-regions on the biological tissue slice.

If two-dimensional distribution of proteins in specific lesioned cells such as cancer cells, or proteins in cells to neighboring cancer cells, or both can be analyzed more precisely by the analytical method of proteins in the biological tissue, such the method can be contributed to development of diagnostic device and drug discovery device.

SUMMARY OF THE INVENTION

It is an object of the present invention to provide a technology for analyzing proteins existing in individual cells of the biological tissue with good accuracy. In particular, it is another object of the present invention to provide a useful technology for fixing a degradation product of tissue on the substrate with maintaining the location information in the biological tissue as a preprocessing for analyzing distribution of proteins in the biological tissue.

The present invention provides a biological tissue processing substrate for fixing proteins in a biological tissue or degradation products of the proteins, the substrate comprising: a porous body that forms a contact surface with the biological tissue, the porous body holding in pores an enzyme for obtaining the proteins or the degradation products of the proteins from the biological tissue, wherein the proteins or the degradation products obtained by the action of the enzyme are brought into contact with a member consisting of a metal.

The present invention provides a biological tissue processing apparatus for fixing proteins in the biological tissue or degradation products of the proteins on a substrate, the apparatus comprising: a substrate holding means for holding the biological tissue processing substrate, an enzyme preparation means for preparing an enzyme in order to obtain the proteins or the degradation products of the proteins from the biological tissue in pores of a porous body that forms a contact surface with the biological tissue in the substrate that is held in the substrate holding means; and a biological tissue contact means for bringing the biological tissue into contact with the contact surface of the substrate having pores in which the enzyme is prepared.

The present invention provides a biological tissue processing method for fixing proteins in a biological tissue or degradation products of the proteins, the method comprising: a step of preparing an enzyme for obtaining the proteins or the degradation products of the proteins from the biological tissue in the pores of the porous body that forms a contact surface with the biological tissue in the substrate; and a step of bringing the biological tissue into contact with the contact surface with the biological tissue of the substrate.

The present invention provides a kit for fixing proteins in the biological tissue or degradation products of the proteins, the kit comprising a substrate composed of the porous body and having a contact surface with the biological tissue; and an enzyme to be supplied to the porous body.

Further features of the present invention will become apparent from the following description of exemplary embodiments (with reference to the attached drawings).

Figure 1:
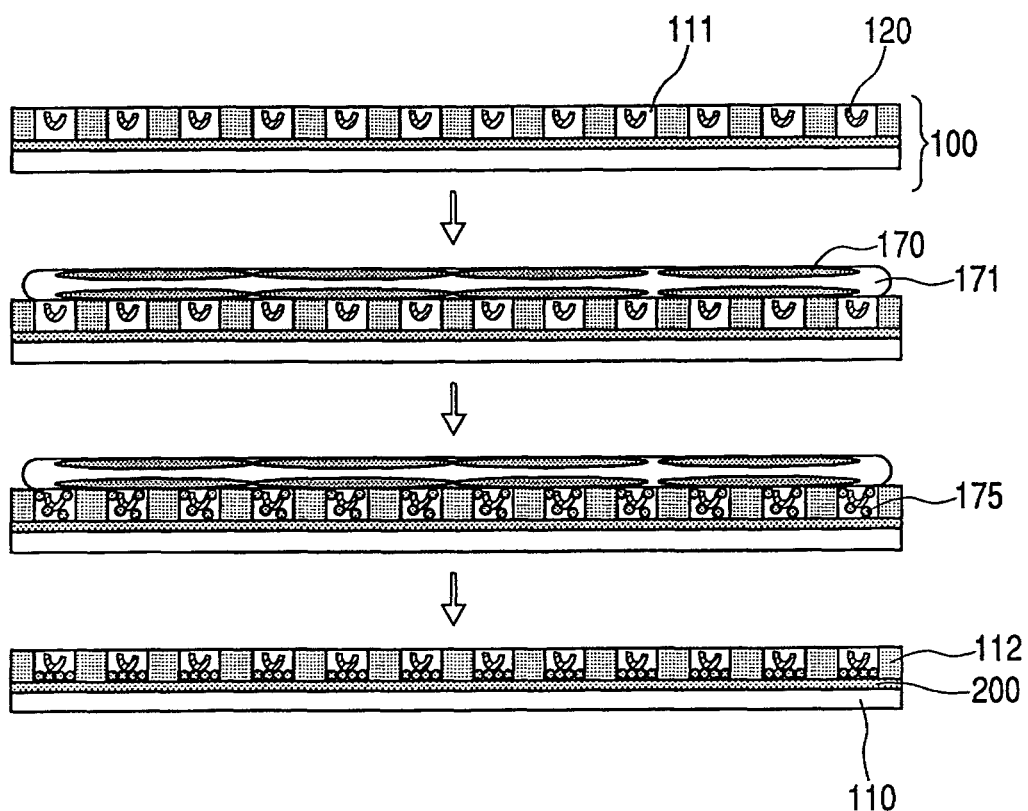
FIG. 1 shows a schematic diagram of a biological tissue processing of the present invention.

Reference numerals found in the drawings denote the following elements or matters. 110 represents support, 111 represents pores. 112 represents porous body (or porous honeycomb film). 113 represents enzyme solution A. 114 represents enzyme solution B. 120 represents enzyme C. 121 represents enzyme D. 122 represents vessel of biological tissue processing apparatus. 123 represents biological tissue processing substrate. 124 represents means for holding biological tissue processing substrate. 130 biological tissue processing substrate moving means. 131 represents position control means of substrate for processing. 132 represents optical observation means. 133 represents means for recording image by optical observation. 134 represents interface. 140 represents droplet discharge head. 141 represents droplet discharge head moving means. 142 represents droplet supply control means. 143 represents biological tissue contacting means. 144 represents biological tissue. 150 represents transfer substrate. 151 represents transfer substrate holding means. 152 represents moving means. 153 represents position control means. 154 represents ink-jet head. 160 represents ink-jet head moving means. 161 represents porous body material dissolving means. 162 represents extracted substance adsorbed on support. 163 represents temperature control means. 164 represents humidity control means. 171 represents biological tissue. 172 represents normal cell. 173 represents lesioned cell. 174 represents signal showing mass peak intensity of degradation product by enzyme A. 175 represents the decomposition product of tissue. 180 represents signal showing mass peak intensity of degradation product by enzyme B. 181 represents signal showing mass peak intensity of eluted protein. 182 represents pores filled with buffer. 200 represents metal.

DESCRIPTION OF THE EMBODIMENTS

Biological Tissue Processing Substrate

The biological tissue processing substrate of the present invention is the substrate for fixing decomposition product of the tissue. The substrate has fixing region, which makes possible to fix the degradation product of the tissue, with maintaining location information thereof in the biological tissue. The fixing region has the contact surface with the biological tissue and the contact surface is formed by the porous body containing at least one type of enzymes. Enzyme is at least fixed within pores of the porous body and, in addition, it may exist on the outer surface (contact surface with biological tissue) of the porous body.

When the biological tissue is contacted with the surface of the fixing region of the biological tissue processing substrate, i.e. a contact surface of the porous body, the enzyme contained in the porous body is reacted with the biological tissue and the degradation product of the tissue is extracted. The thus extracted degradation product of the tissue is incorporated into pores and is fixed within the fixed region of the substrate. In the substrate of the present invention, the degradation product is composed so as to contact with member consisting of metal. The member consisting of the metal has an action to increase ionization efficiency of the protein, when the protein is measured by TOF-SIMS (time of flight secondary ion mass spectrometry). More particularly, entwining the peptide chain of protein molecules in the biological tissue could be factors for low generation efficiency of the secondary ion species of proteins in case of measurement using TOF-SIMS. Consequently, the substrate of the present invention is constructed such that the degradation product makes contact with metal having an effect to increase ionization efficiency of the protein. This makes to increase generation efficiency of secondary ion species derived from protein molecules. Example of concrete metal member is the member containing gold (Au) or silver (Ag), and a member coating the film containing such metal on the support, or the porous body itself containing such metal particles can be mentioned.

The decomposition product of the tissue can be fixed on the substrate with maintaining the location information of proteins in the biological tissue under high ionization efficiency.

FIG. 1 shows a structure of substrate 100, in which a covering layer of the porous body 112, which forms contact surface with the biological tissue 171 on the top surface of the support 110, is formed, and enzyme 120 is fixed within the pores 111 of the porous body. Further, fixing process of the decomposition product of the tissue 175 using the substrate 100 is schematically shown. In FIG. 1, metal member 200 having increasing action of ionization efficiency of the protein is disposed on the support 110, and the porous body 112 is disposed on the metal member 200.

Cells 170 in the biological tissue 171 are eluted as proteins or degradation products 175 into the pores by contact with enzyme 120 in the pores, and the proteins or the degradation products 175 are fixed on the substrate 100 under the condition contacting with the metal member 200.

Consequently, the substrate for processing the biological tissue of the present invention can be preferably used as the substrate for preprocessing in analysis of the protein in the biological tissue. Further, when TOF-SIMS is applied as the analytical instrument, macroscopic observation of the two-dimensional distribution of the decomposition product of the tissue can be possible by imaging mass spectroscopic results with high spatial resolution.

The biological tissue can be any population of biological cells. It can be lesion biological tissue slices. Specifically, a region for obtaining information on the protein can be specific cells in the lesion biological tissue slice.

According to the present invention, the decomposition product of the tissue can be fixed on the substrate under the condition to facilitate ionization with maintaining the location information of the protein in the biological tissue, in fact, in what region or in what cells in the biological tissue, the specific protein is distributed.

Each element composing the substrate for processing the biological tissue will be explained hereinbelow.

(Composition of Substrate)

With regard to the material for forming fixing region of the decomposition product of the tissue in the substrate, any materials having physicochemical properties for maintaining fixing condition of the decomposition product of the tissue can be used. Consequently, materials for composing the substrate or forming the substrate can be appropriately determined depending on the condition such as fixing method of decomposition product of biological tissue and analytical method performed later.

Composition of the substrate is such that the composition formed with the porous body (layer) on the support and the composition with the porous body in the whole substrate can be utilized. In case that the support (part) and the porous body (part) are constructed integrally or the substrate is totally constructed with the porous body, material of the suitable for holding enzyme may be selected as the construction material. Fixing method of the degradation product of the tissue to the fixing region of the substrate can be selected from physical adsorption such as electrostatic interaction, hydrophilic interaction, hydrophobic interaction or the like, chemical adsorption such as covalent bonding and others may be used.

For example, when the substrate is composed of the support having the fixing region on the surface and laminating the porous body on the fixing region, a part of fixing region of the support is subjected to surface-treatment to make the surface as hydrophobicity. This substrate composition can be preferably utilized when analytical method of protein is performed by TOF-SIMS. In this case, considering functions as the substrate, preferable metal for second ionization, e.g. gold or silver, is preferably used as the composition material of the support. Further, mass resolution at the detection can be improved by using flat surface support. In this case, the support is not necessary to be gold or silver as a whole, and the support obtained by depositing gold or silver on the flat surface of appropriate substrate can be used. The support with such the composition is more preferable from the viewpoint of manufacturing cost. Further, in case that analytical means is time of flight mass spectrometry (TOF-MS), the support of carbon, porous silicon, mesh for electron microscope, etc. can be preferably used from the standpoint of ionization. High detection sensitivity of TOF-MS is known to be obtained by using the carbon such as black carbon or carbon powder. As such, proper material for analytical use applied later can preferably be selected.

In addition, in the substrate composition using the above-mentioned support, from the standpoint of improved efficient anchorage of the degradation product of the tissue, material, which fixes decomposition product of the tissue more easily or has higher fixing strength than the material of the porous body, is preferably used at least as the material constructing the surface for the fixing region of the support.

As explained above, the substrate can employ the composition constructed totally with porous body (an integrated type in which the support is also the porous body) or the composition in which the porous body is disposed on a predetermined position of a surface of the support. Proviso that the metal member for increasing the ionization efficiency of protein is essentially located to contact with the protein or the degradation product obtained by the action of enzyme. The composition disposing the porous body on the support may be the composition the support is integrated with the porous body or the separation type in which the support can be separated from the porous body. For example, in case that a planarity of the substrate is not important for analysis used later in microscopic observation, etc., the support is preferably the integrated type in which the support is also the porous body and is convenient on manufacture and application. In case that planarity of the substrate is important as like in TOF-SIMS, the separated type, in which the porous body can be separated from the surface of the support, is preferable. Further, the separated type support has preferably flat contact surface with the porous body. Planarity of the support surface results to perform analysis with high mass resolution condition, for example, in TOF-MS analysis.

(Porous Body)

The contact surface, which is in contact with the biological tissue, for fixing the degradation product of the tissue to planarly spread fixing region is formed with the porous body. In the aforementioned integrated type, in which the support is used as the porous body, the fixing region, which is planarly spreading degradation product of the tissue, is formed with the porous body itself. On the other hand, in the separate type using the support surface as the fixing region, pores of the porous body has the function of pathway for transferring the degradation product of the tissue from the contact surface side with the biological tissue to the surface of the support. Enzyme for extracting the degradation product of the tissue from the biological tissue is contained at least in pores of the porous body, and may also exist on the outer surface of the porous body. Roles of the porous body are to contact the enzyme with the biological tissue in the precise position and to fix the degradation product of the tissue in the fixing region spreading for surface direction of the substrate in the precise position. Enzyme is maintained with dry state or solution in the porous body, and when the biological tissue is processed, it is used in the state of aqueous solution. Consequently, material of the porous body should have property of water resistance and not inhibit enzymatic activity, i.e. using material without having inhibitory action or without giving substantial effect to the enzyme, if inhibition occurs. The surface of the porous body may also be covered by such the material. Examples of composition of the porous body are organic material, inorganic material, metal, metal oxide and ceramics, or composite material composed of two of them or more, but are not limitative. Pores surface of the porous body is preferably hydrophilic. Hydrophilicity makes easy to introduce solution and holding, and is preferable for use in the state of aqueous solution of enzyme. In addition, wall surface of pores of the porous body may contain material for stabilizing enzyme and may also contain functional group and linker for fixing the enzyme. In case that the substrate is the integrated type consisting of the porous body alone, the substrate per se can be the support for fixing the degradation product of the tissue and is preferably hydrophobic.

As described above, the porous body may be an integration type in which the porous body is also the support or a separation type in which the porous body can be separated from the support.

When the porous body is an integration type, the degradation product of the tissue is fixed on the surface of the porous body. Consequently, the surface of the porous body is preferably material appropriate for fixing the degradation product of the tissue. However, the metal member for increasing ionization efficiency of the degradation product obtained by the action of enzyme and the degradation product of the tissue should be disposed to contact with each other. For that reason, the porous body per se is required to compose with a member containing metal.

On the other hand, when composition of the separate type is selected, the degradation product of the tissue is fixed on the metal layer formed on the support after passing through pores of the porous body. Consequently, the surface of the porous body is preferably the surface, on which the degradation product of the tissue is difficult to fix as compared with the metal layer on the support. In the latter case (in case of separate type), the porous body is used such that it has porous structure likely to fix the degradation product of the tissue after passing through the porous body and arriving at the surface of the metal layer located underneath thereof.

Pore size of the porous body is preferably ranging from 100 nm to 10 μm. When the pore size is 100 nm or more, enzyme can be efficiently incorporated into pores. When the pore size is more than 10 μm, pore size and size of cells may be equal or more, and as a result, degradation products of the biological tissue extracted from plurality of cells are more likely to pass a pore. More preferable pore size is ranging from 1 μm to 10 μm when taking into consideration a liquid to be supplied to the pores.

A structure of fine pores of the porous body may have the structure such that the enzyme can be contact with the biological tissue in good accuracy of position and the decomposition product of the tissue can be fixed in the fixing region of the substrate with good accuracy of position. In case of the above separate type, pores may be passing from the top surface (the "top surface" herein means the contact surface on the side contacting with the biological tissue) to the contact surface between the porous body and the metal layer, and any structures can be applied. Examples of various compositions of the substrate depending on disposed embodiments of the porous body are shown in FIGS. 2A to 2H as schematic sectional views to the thickness direction of the substrate. For example, the porous body 112 in FIG. 2A has the form of thin plate or thin layer (thin film) having net-like structure disposed on the metal layer 200 formed on the support 110. Numeral 111 indicates pores constructing the porous body.

Even in such the structure, if the structure has sufficiently dense structure or the porous body has sufficiently thin structure, the degradation product of the tissue can be fixed on the metal layer on the support before the degradation product of the tissue is too much spread over the two-dimensional plane direction in the porous body. Further, the pore structure is preferably the structure having each independent pore. As like in FIG. 2B, when each pore is located independently without linkage, accuracy of location information can be improved by suppressing expansion to the two-dimensional planar direction.

Figure 2A:
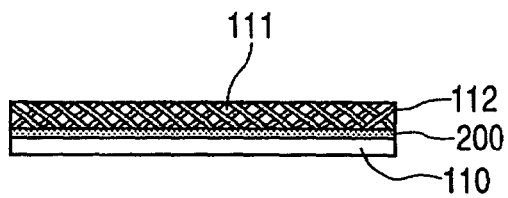
FIGS. 2A, 2B, 2C, 2D, 2E, 2F, 2G and 2H shows an explanatory diagram of the support and the porous body of the present invention.
Figure 2B:
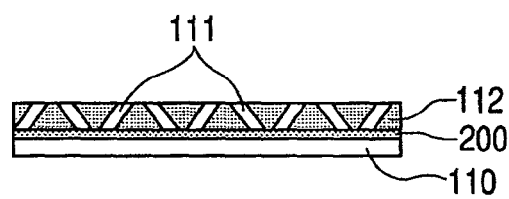
Figure 2C:
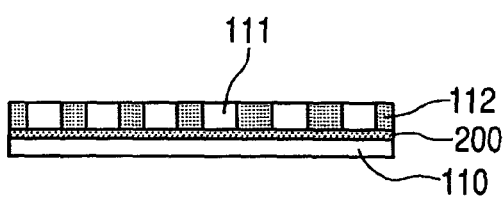

In addition, pores are preferably extended to the direction of thickness of the support, i.e. a direction crossing to the surface of the support, especially to the vertical or almost vertical direction against the surface of the support of planar surface as shown in FIG. 2C. When pores are standing with vertical or nearly vertical angle, the degradation product of the tissue can be reached to the support rapidly and accuracy of the location information is can be improved much more.

Figure 2D:
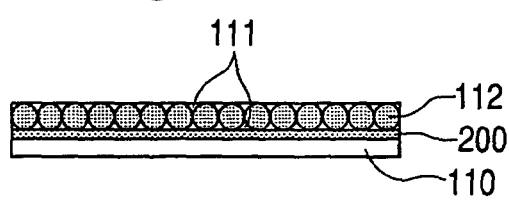
Figure 2E:
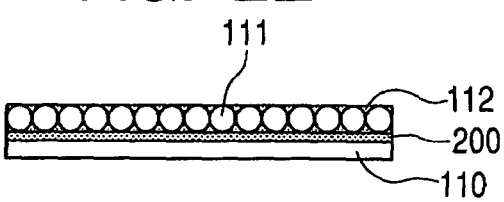
Figure 2F:
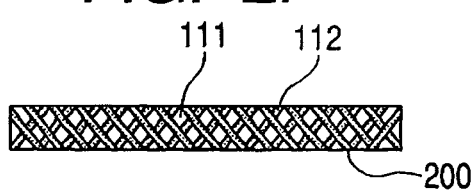
Figure 2G:
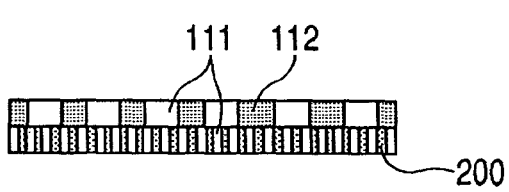
Figure 2H:
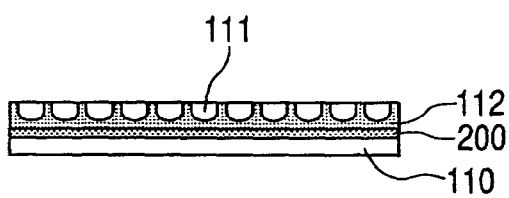

The porous body as explained hereinabove can be formed by general patterning technology. For example, what is called semiconductor processing technology such as photo lithography, electron beam lithography, X-ray lithography, etc. or laser processing technology and machining technology can be used. Furthermore, various methods, for example, not only the top-down approach technology but also fine pattern formation technology by applying phase separation of polymer or inorganic substance, pore formation technology by anodic oxidation of metal, pore formation technology by utilizing a mold such as water droplets and surface active agents can be utilized. Further, as shown in FIG. 2D, aggregate of fine particles are used as a porous body 112 and space of grain boundary can be used as pores 111. Conversely, as shown in FIG. 2E, porous body 112 having global pores 111 can be used. Furthermore, as shown in FIG. 2F, the porous body and the support may have a construction consisting of pores having identical form (i.e. the substrate is totally consisting of the porous body). As shown in FIG. 2G, a perforated metal member 200 is used as the support 110 and the porous body having pores of different size may be disposed. In addition, the substrate can be prepared by such that the substrate, on which fine particles are arranged and fixed, is pressed onto the porous material layer to prepare pores, i.e. fine particle imprinting method. In this case, regular porous body can be formed as shown in FIG. 2H.

In case that a solution exists in pores of the porous body, from the standpoint of maintaining enzyme activity indicated hereinbelow, condition for storage and delivery is preferably frozen condition.

(Enzymes)

An enzyme contained in the porous body can be the enzyme which can be utilized for extracting the degradation product of the tissue from the biological tissue. For example, any enzymes which can decompose biological tissue components can be used. Examples thereof are preferably protease or lipid degrading enzyme. Since proteins or lipids occupying majority of components of cell membrane can be decomposed, the degradation product of the tissue can be extracted in the liquid.

Among them, enzyme is preferably endopeptidase. According to such embodiment, even if cell membrane is not decomposed, exposed parts of membrane protein on the surface of cell membrane can be decomposed. Endopeptidase is a generic term of peptidase, an enzyme acting on the peptide bond within the peptide chain and fragmenting it, and can also have an action on the peptide bond containing terminal amino acid residue. Generally, endopeptidase is classified into following four groups according to the type of catalytic residue of active site.

(1) Serine protease (trypsin, chymotrypsin, etc.)
(2) Cysteine protease (papain, bromelain, cathepsin B, etc.)
(3) Aspartic protease (pepsin, chymosin, cathepsin D, etc.)
(4) Metalloprotease (thermolysin, etc.)

Endopeptidase having properties of more than two groups in above is also known.

Furthermore, a combination of lipid degrading enzyme and protease is preferable, because degradation of processing can also be reduced.

With regard to lipid degrading enzyme, lipase, phospholipase, cholesterol esterase, sphingomyelinase and various types of esterase can be mentioned. Among them, examples of lipase which can be mentioned are lipase derived from microorganisms such as genus *Rhizopus* having excellent positional selectivity, genus *Aspergillus*, genus *Mucor*, genus *Geotrichum* having specificity to fatty acid, genus *Candida* indicating no specificity, genus *Pseudomonas*, genus *Penicillium*, genus *Chromobacterium*, etc. and lipase from animal origin such as pancreatic lipase. Among them, as for lipase exhibiting readily increasing synthetic activity, lipase derived from genus *Rhizopus*, genus *Mucor* and genus *Chromobacterium* having strong activity for alkyl group having longer than middle chain is more preferable. Example of cholesterol esterase is an enzyme derived from microorganism such as genus *Candida*. Examples of phospholipase are enzymes derived from plant such as cabbage, peanuts, carrot, etc., those derived from microorganisms such as genus *Streptomyces*, etc. and enzymes derived from *Bryophyta* (moss).

Examples of protease other than those above are: serine protease such as plasmin, kallikrein, thrombin, factor Xa, acrosin, enteropeptidase, urokinase, cocoonase, premonophenol monooxygenase activation enzyme, *E. coli* protease II, chymotrypsin A, chymotrypsin B, chymotrypsin C, *Meiridium* proteinase A, *E. coli* protease I, cathepsin G, elastase, α-lytic protease, thermomycolin, proteinase K, *Streptomyces griseus* protease 3, Staphylococcal proteinase, *Tenebrio* α-proteinase, *Arthrobacter* serine proteinase, thermophilic *Streptomyces* alkaline proteinase, *Alternaria* endopeptidase,

*Candida lipolylica* alkaline proteinase, subtilicin, mouse submaxillary protease, other microbial serine protease and snake venom thrombin-like enzyme; for example, thiol protease such as cathepsin B1, papain, ficin, bromelain, chymopapain, *Clostridium histolylicum* proteinase B, Streptococcal proteinase, cathepsin L, yeast proteinase B, protease in albumen of germinant corn, cathepsin S and PZ-peptidase; for example carboxyl peptidase such as pepsin A, B, C, cathepsin D, renin, chymosin, yeast proteinase A, cathepsin E, penicillopepsin and other microbial; carboxyl protease; for example metalloprotease such as collagenase, *Sepia officinalis* protease, renal neutral endopeptidase, snake venom proteinase, *Bacillus subtilis* and *Bacillus thermoproteolyticus* protease, A. *Myxobacter* AL-1 protease II, B. *Armilliaria mellea* protease, other microbial metalloprotease and echinoid hatching enzyme; for example other endopeptidase such as other intracellular protease, *Bacillus sphaericus* protease, Russell's viper venom factor X activation enzyme, *Echis carinalusvenom* prothrombin activating enzyme, post-proline cleaving enzyme and seminine; for example aminopeptidase such as leucine aminopeptidase, particulate aminopeptidase, aminopeptidase B, small intestine surface aminopeptidase, yeast aminopeptidase I, *Aspergillus* aminopeptidase, aminoacylproline aminopeptidase, *Bacillus stearothermophilus* aminopeptidase, *Clostridium histolyticum* aminopeptidase, *Aeromonas* aminopeptidase, *Streptomyces griseus* aminopeptidase, *Trilirachium album* Limber aminopeptidase K, acylamino acid liberating enzyme and pyrrolidonyl peptidase; for example carboxypeptidase such as carboxypeptidase C, carboxypeptidase A, carboxypeptidase B, phaseoline, carboxypeptidase Y, *Aspergillus* acidic carboxypeptidase, proline carboxypeptidase (angiotensinase C), cathepsin A cathepsin B2, carboxypeptidase N, penicillocarboxypeptidase, *Streptomyces griseus* K1 carboxypeptidase, germinant barley carboxypeptidase, cotton seed carboxypeptidase and carboxypeptidase P; and for example dipeptidyl peptidase such as angiotensin I converting enzyme, *E. coli* dipeptidyl carboxypeptidase, cathepsin C (dipeptidyl aminopeptidase I), X-prolyl-dipeptidyl aminopeptidase, dipeptidyl aminopeptidase II and dipeptidyl aminopeptidase III.

More preferably, protease as ficin, bromelain, pepsin, parapepsin I, parapepsin II, papain, trypsin, chymotrypsin, plasmin, Orientase, Newlase, protine A, denapsin, protease, chymosin, rennin, Pancreatine, elastase, carboxypeptidase, aminopeptidase and other acidic protease or alkaline protease can be mentioned. Combination of enzymes is quite naturally not limited in the above.

Enzyme contained in the porous body may be dissolved condition in liquid or dried condition. When the enzyme is contained in pores with dissolved condition, since the biological tissue can be processed by contacting with directly in that condition, it is easy to operate.

Any method for containing enzyme with dry state in the porous body can be selected. For example, after introducing the enzyme solution into porous pores by any method such as injection method hereinafter explained and subjecting to lyophilization, enzyme can be stored with dried condition in the pores. The biological tissue processing substrate, in which the enzyme is stored in dry condition as just described, is quite stable and can be stored for quite a while. When the enzyme is contained with dry state in the pores, the substrate can be used by such that droplets are injected directly into the pores and the enzyme is made to function.

With regard to generation means for droplets, similar method as like the injection method of enzyme herein below explained may be applied.

Enzyme concentration in pores can be selected from any concentration, if it has little influence on detection of proteins after processing the biological tissue, and may be determined from size and depth of porous body and reaction time. If concentration of enzyme is higher than that of the degradation product of the tissue, care should be taken, since it causes to increase noise in detection after processing.

Figure 3A:
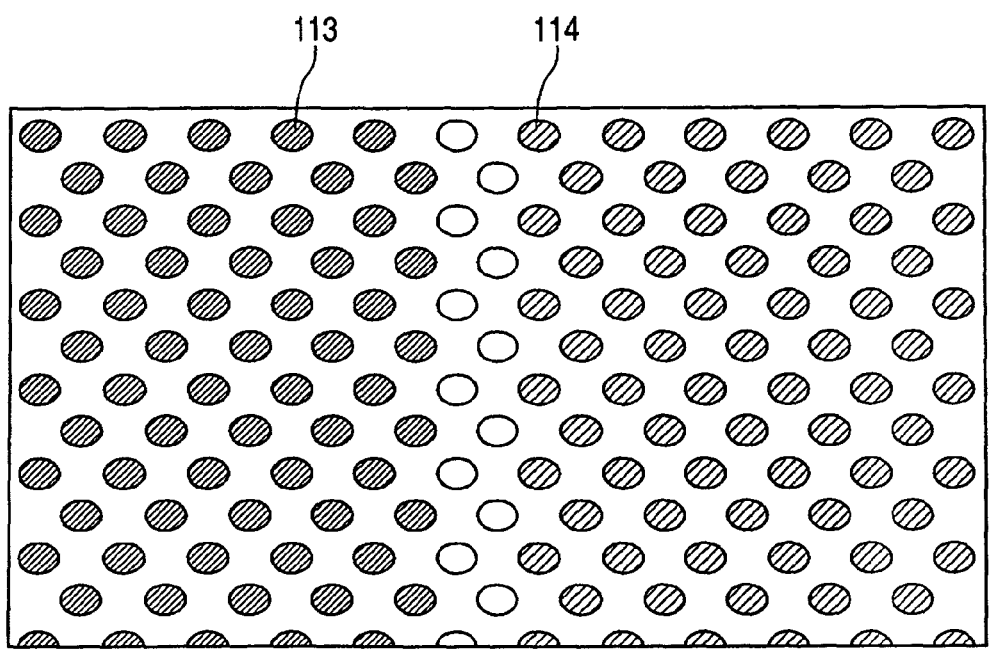
FIG. 3A shows a top view and FIG. 3B a sectional view of the substrate, in which two types of enzyme solution are held in separate fine pores, for processing biological tissue of the present invention.
Figure 3B:
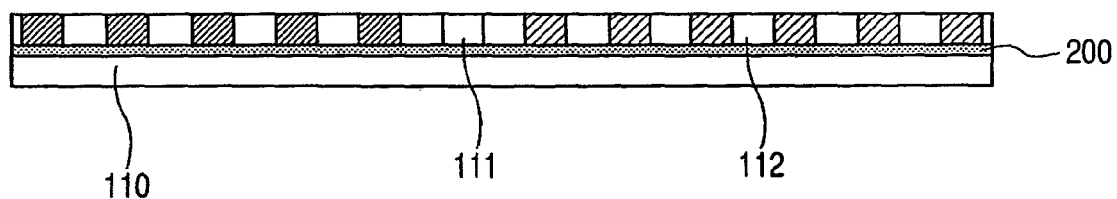
Figure 4A:
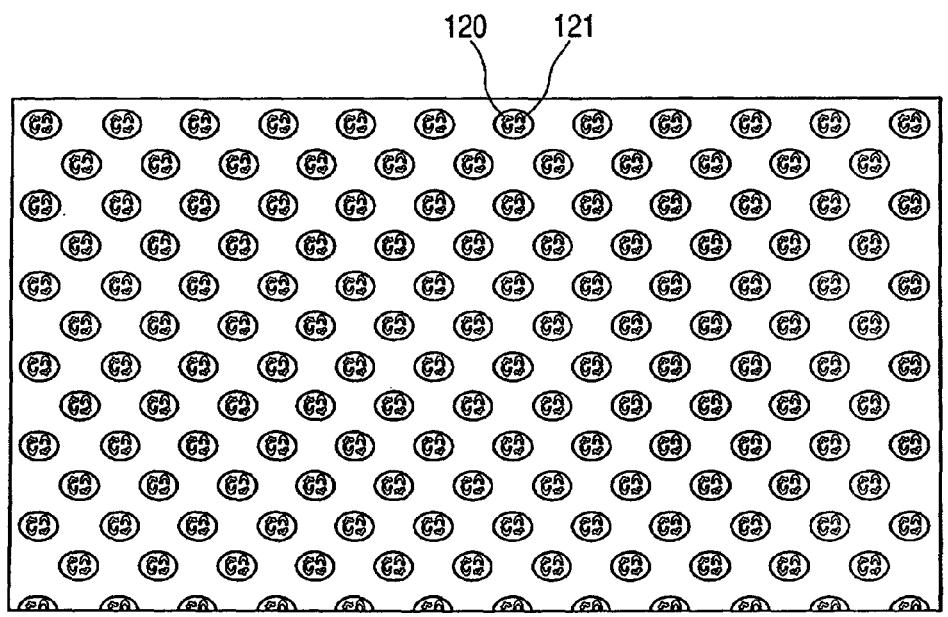
FIG. 4A shows a top view and FIG. 4B a sectional view of the substrate, in which two types of enzyme are held in each fine pore, for processing biological tissue of the present invention.
Figure 4B:
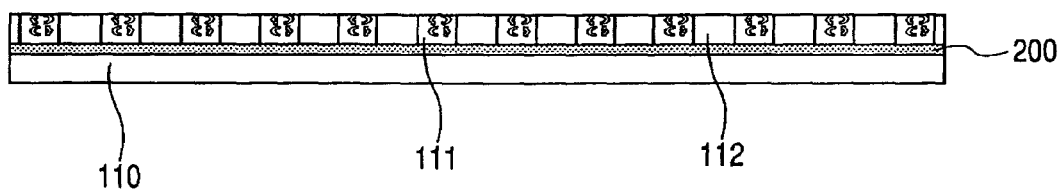

In case of having plurality of enzymes in the porous body, as shown in FIGS. 3A and 3B, different enzyme (solution) 113, 114 can be contained within pores 111 in the positionally separated regions of the porous body 112 on the support 110, and in this case plurality of peptide fragments can be obtained in the different region on the same substrate. As shown in FIGS. 4A and 4B, plural type of enzymes 120 and 121 in each pore 111 of the porous body 112 on the support 110 can be contained, and in this case, the biological tissue can be decomposed simultaneously by plural methods.

(Biological Tissue Processing Apparatus)

Biological tissue processing apparatus of the present invention is the biological tissue processing apparatus for fixing the degradation product of the tissue in the biological tissue on the substrate having composition described as above. This processing apparatus has means for holding the substrate disposing a part consisting of the porous body on the surface and means for supplying solution into the held substrate.

According to such embodiment, when the porous body in the substrate does not contain enzyme, enzyme solution can be supplied to a part of the porous body on the substrate by supplying means of solution. Further, when the substrate contains enzyme in dry state, enzyme held in the substrate can be dissolved to the solution appropriate for processing the biological tissue. Consequently, in any case when either substrate hereinbefore described is used, the substrate which is able to process biological tissue can be prepared by the solution supplying means. Furthermore, in case of pretreatment for mass spectrometry, a component required for analysis can be arranged previously by supplying solution; such as matrix and sensitizer necessary for increase in sensitivity by utilizing means for supplying solution.

The biological tissue processing apparatus of the present invention has preferably means for recording location information by reading image information of the substrate. According to such embodiment, pores of the biological tissue processing substrate held by holding means of the processing apparatus is recognizable. With regard to means for reading image information, optical microscope and CCD camera can be concretely mentioned without limitation. In addition, means for recording the location information may be such like personal computer.

Further, means for supplying solution is preferably means using ink-jet system. According to such embodiment, fine droplets can be rapidly supplied to the required region on the substrate.

Further means for observing the biological tissue processing substrate and recording the location information is employed, and mans for supplying solution is means using ink-jet system, then in such the case, solution supply of high precision can be performed by coupling with such two means. Namely, droplets can be supplied accurately to the targeted small area by recognizing pores of the biological tissue processing substrate. Further, this solution supply means can be utilized usefully for supplying matrix and sensitizer necessary for mass spectrometry.

With regard to means for contacting the biological tissue onto the surface of the biological tissue processing substrate installed in the biological tissue processing apparatus of the present invention, various compositions can be utilized. Concretely, an operation for contacting the biological tissue onto the desired position of the biological tissue processing substrate can be performed continuously from the supply of droplets by installing the built-in means, which can conduct the operation of biological tissue, such as manipulator.

Means for contacting the biological tissue which can mentioned, without limitation, is (1) means for contacting directly the biological tissue onto the porous body and (2) means for transfer the biological tissue, which is supported previously by the other substrate for transfer, onto the biological tissue processing substrate. In this respect, the substrate for supporting the biological tissue is designated as the other substrate (hereinafter referred to as "transfer substrate") in the present invention. As for material of the transfer substrate, conventional polymer material can be used and exemplified as LDPE (low-density polyethylene). Consequently, means for contacting the biological tissue may be means for contacting the biological tissue on the transfer substrate onto the biological tissue processing substrate. According to such embodiment, a protein in the biological tissue is transferred with good accuracy of position and the degradation product of the tissue can be extracted. When material, in which the biological tissue is more easily-absorbable than material of the porous body, is used as the material of the transfer substrate, the biological tissue can be mostly removed simultaneously finishing the transfer from the biological tissue processing substrate. Consequently, since substance causing noise can be removed, the degradation product of the tissue can be detected with high S/N ratio.

The biological tissue processing apparatus of the present invention has preferably temperature control means and/or humidity. The first advantage is that function of enzyme can be utilized maximally by maintaining optimum temperature to the enzyme activity involved in processing the biological tissue in the processing region. The second advantage is that vaporization of liquid can be prevented by maintaining at constant humidity after supplying fine droplets into pores of the porous body.

In addition, the biological tissue processing apparatus of the present invention has preferably means for removing the porous body disposed on the biological tissue processing substrate. Concrete examples of removing method using such means are: (1) removing the porous body from the support by peeling off; and (2) removing from the porous body by using solvent alone. Since sample adsorbing the decomposition product of the tissue on the substrate having high planarity can be supplied, it is quite; advantageous for obtaining high mass resolution by time-of-flight mass spectrometry.

According to the removing method (1), when either the surface of the porous body or that of the support is prepared by material such as PDMS having superior adhesiveness with other substrate, the porous body and the support can be separated optionally. According to the removing method (2), the porous body can be removed with fixing the degradation product of the tissue on the support by using solvent which can dissolve material of the porous body but can not dissolve the degradation product of the tissue. Accordingly, two-dimensional distribution of the degradation product of the tissue on the support can be maintained. Examples of solvent hereinabove described are, without limitation, ethyl acrylate, butyl acrylate, acetone, amyl alcohol, isopropyl alcohol, isopropyl ether, ethanol, oleic acid, amyl acetate, isopropyl acetate, ethyl acetate, butyl acetate, prolyl acetate, methyl acetate, diisopropyl ketone, diethyl ether, cyclohexanol, cyclohexene, dibutyl ether, dibutyl phthalate, dibenzyl ether, butyl stearate, Cellosolve, tricresyl phosphate, tributyl phosphate, toluene, hexane and methyl isobutyl ketone. Even if the solvent dissolve the degradation product of the tissue, the degradation product of the tissue is very small amount to the adsorption surface, and if the solvent does not dissociate binding between the support and the degradation product of the tissue, two-dimensional distribution of the degradation product of the tissue on the support can be maintained in a similar manner. Further, method for removing the porous body is not limited within the above.

As a result of having above indicated respective means, after performing operation from maintaining the biological tissue processing substrate to removing the porous body, since immediate supply of matrix and sensitizer necessary for mass spectrometry can be performed, the operation from the biological tissue processing to the sample preparation can be continuously performed.

The biological tissue processing apparatus of the present invention is further preferable to have means for centrifugally treating the biological tissue processing substrate in a condition when the solution is held in pores of the porous body. In addition, centrifugal treatment is preferably performed to the direction of thickness of the substrate.

According to this embodiment, extracted protein or degradation product of the extracted protein can be adsorbed onto the substrate by centrifuging the biological tissue processing substrate directly, and as a result, time for processing biological tissue can be shortened.

Figure 5A:
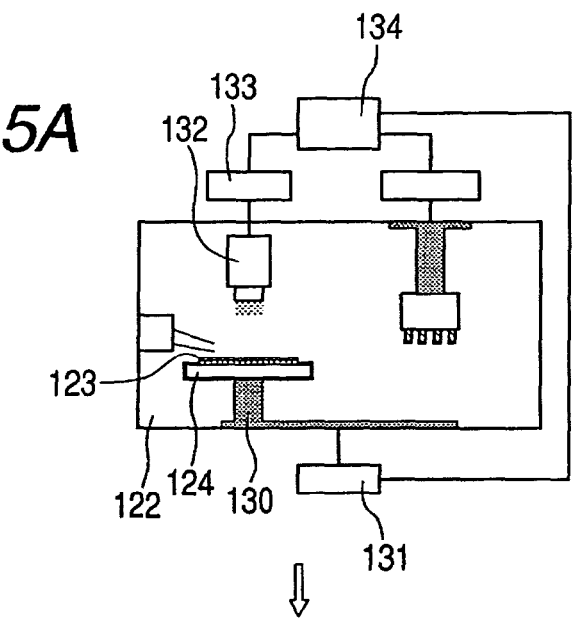
FIGS. 5A, 5B and 5C shows an explanatory diagram of a biological tissue processing apparatus of the present invention.
Figure 5B:
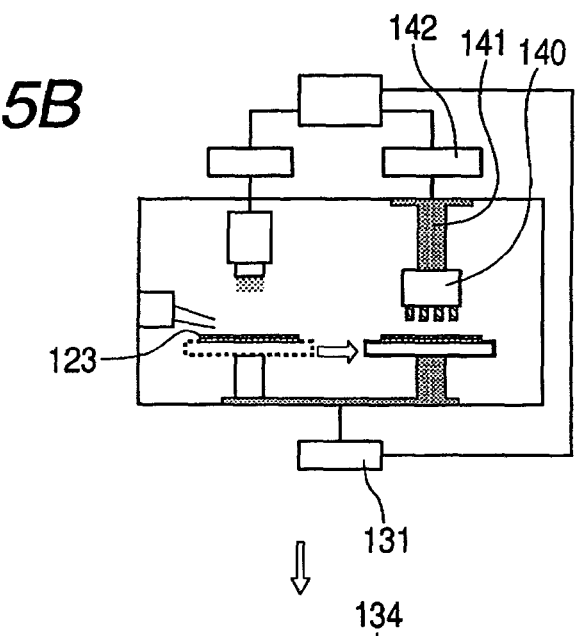
Figure 5C:
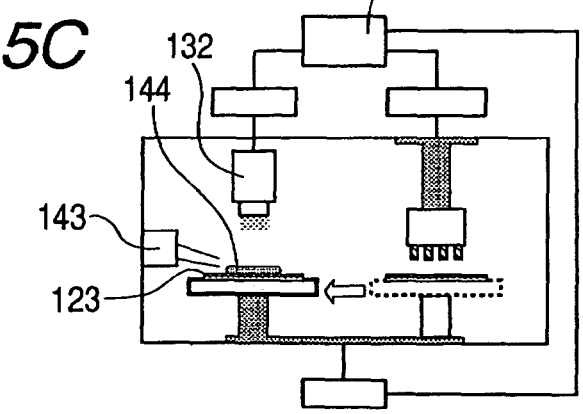

One embodiment of the biological tissue processing apparatus of the present invention is shown in FIGS. 5A to 5C.

In a case 122 of the biological tissue processing apparatus in FIG. 5A, means 124 holding the substrate 123 for processing biological tissue is fixed on the means for transferring the substrate 130 and is able to displace by position control means of the substrate 131. Further, a position of pores on the substrate 123 can be recognized by disposing means 132 for optically observing the substrate 123 and means 133 for recording the optically observed image. Image processing of the image is performed by interface 134 and a position for supplying droplets can be determined.

On the other hand, as shown in FIG. 5B, on the substrate 123, which was displaced by the substrate position controlling means 131, head for supplying droplets 140 is placed and is coupled with droplets supply head displacement means 141 and droplets supply control means 142. Interface 134 is connected to substrate position control means 131 and droplets discharge head position control means 140, and position adjustment of the substrate 123 and head for supplying droplets 140 can be made. According to such operation, droplets can be supplied accurately and exactly into pores of the porous body of the substrate. In this apparatus, enzyme preparation means for preparing enzyme and solution for enzyme reaction at least in pores of the porous body is composed of the head for supplying droplets 140 with the droplets supply head displacement means 141 and the droplets supply control means 142. Solution for enzyme reaction is to supply environment for the enzyme reaction required for preparation of the decomposition product of the tissue (protein and/or degradation product of protein) from the biological tissue by an enzymatic action. Various components for expressing enzymatic activity or enhancing enzymatic activity and having required pH, salt concentration, etc for enzyme reaction can be contained depending on need. Various buffers can be utilized as such solution.

Further, as shown in FIG. 5C, the biological tissue 144 can be contacted onto the substrate 123 using the biological tissue contact means 143 after transferring again the substrate 123 to the position, which can be observed by using optical observation means 134, while observing the condition by using optical observation means 132. Any means for contacting with the biological tissue 143 may be employed, and is preferably means for operating micro-substance such as manipulator.

In FIGS. 5A to 5C, a composition such that means for holding substrate 124 can be transferred from the position under optical observation means 132 to the position under means for supplying solution 140, is shown. However, other composition wherein means for holding substrate 124 is fixed and optical observation means 132 and means for supplying solution 140 thereby performing similar motion can be employed.

Figure 6:
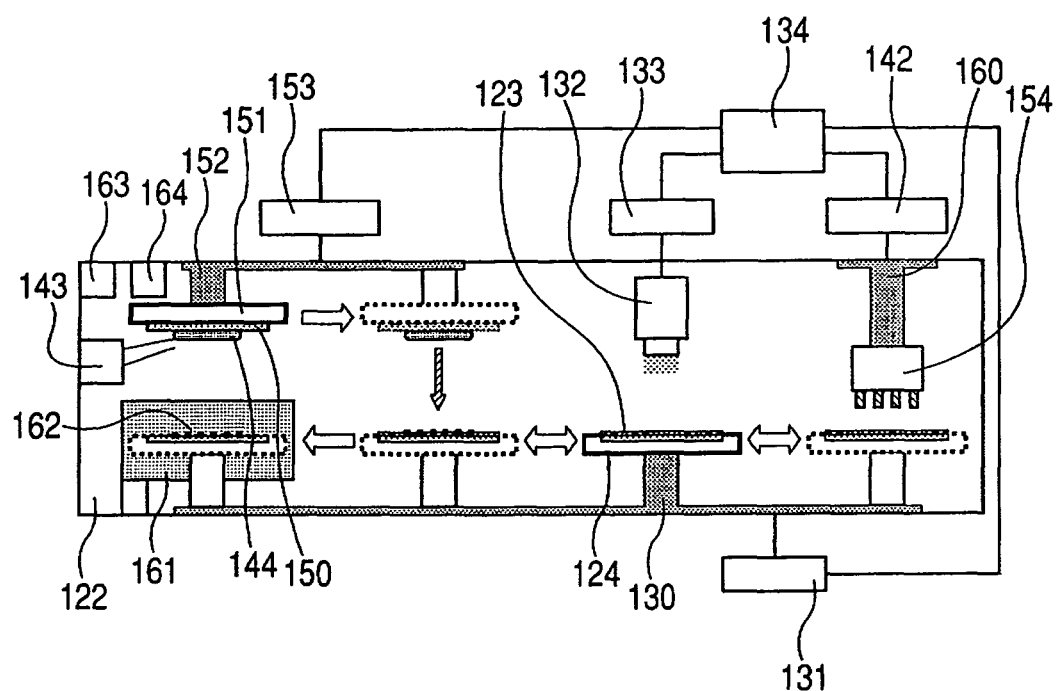
FIG. 6 shows an explanatory diagram of a biological tissue processing apparatus of the present invention.

In addition, preferable biological tissue processing apparatus of the present invention is shown in FIG. 6. The biological tissue processing apparatus shown in FIG. 6 has a transfer means necessary for using transfer substrate 150 other than the substrate 123 for processing biological tissue. The transfer means has means 151 for holding transfer substrate 150, means for transfer 152 and position control means 153.

In FIG. 6, transfer substrate 150, means for holding thereof 124, 151 and means for transfer 130, 152 shown by solid line are condition in initial step of the process. The degradation product of the tissue is extracted into pores by the action of enzyme as a result of approaching closely the transfer means to the means for holding substrate 124 with holding the substrate 123. Since the biological tissue in total is a condition attaching to the transfer substrate, possibility for entering impurities causing noise is very low and the degradation product of the tissue is detected with high S/N ratio.

In addition to the above described embodiment of the apparatus as shown in FIGS. 5A to 5C, the apparatus shown in FIG. 6 has means having the droplets supply method of the ink-jet method, means for removing the porous body and temperature control means and humidity in the case of biological tissue processing apparatus.

Effect obtained by each added means described above is as follows.

Introducing the ink-jet system in the droplet discharging method is made possible to supply droplets into smaller target region. Ink-jet head 154, means for transferring ink-jet head 160 and droplet supply control means 142 are connected. As a result, alignment of the biological tissue processing substrate 123 controlled by interface 134 and ink-jet head 154 can be made.

The biological tissue 144 on the transfer substrate 150 is disposed on the substrate 123 by biological tissue contacting means 143 and contacts therewith. In the case 122, temperature control means 163 and humidity control means 164 is installed.

The porous body can be immediately removed after adsorbing the decomposition product of the tissue by installing means for removing porous body in the processing apparatus. Concretely, porous body material dissolving means 161 can be mentioned as shown in FIG. 6. To this means the solvent is poured to dissolve material of the porous body by immersing the biological tissue processing substrate adsorbed with the decomposition product of the tissue previously for necessary time.

When the solvent, which dissolves material of the porous body well and does not dissolve the decomposition product of the tissue or does not affect to the adsorption between the decomposition product of the tissue and the support, is used, the decomposition product of the tissue 162 adsorbed on the support is remained on the support after the treatment.

Other means for removing porous body which can be mentioned are means for peeling off the porous body and the support, decomposition means by laser, means physically grinding down from top surface of the porous body, etc.

As a result of installing temperature control means and humidity 63 and 64 in the case of biological tissue processing apparatus, enzymatic function involving biological tissue processing can be utilized as maximum as possible. In addition, liquid state can be maintained without vaporizing fine droplets attached on the substrate for the processing.

Using the composition other than the composition for contacting the biological tissue to the substrate in apparatus shown in FIGS. 5A to 5C and FIG. 6, manufacturing apparatus of substrate used for contacting biological tissue can be constructed.

(Biological Tissue Processing Method)

A method for processing biological tissue of the present invention has a process preparing enzyme in pores of the porous body in the substrate which forms contact surface with the biological tissue, and a process contacting the biological tissue to the contact surface of the substrate with the biological tissue.

According to such embodiment, processing the biological tissue and fixing the decomposition product of the tissue in the biological tissue to the support can be performed.

Methods for contacting the biological tissue which can be mentioned are (1) method for directly contacting the biological tissue on the porous body and (2) method for transferring the biological tissue supported on the transfer substrate to the substrate for processing the biological tissue, but are not limited.

Method for processing biological tissue of the present invention has preferably a process supplying solution to the biological tissue processing substrate. According to such embodiment, when the biological tissue processing substrate holding enzyme in dry state is used, the enzyme can be dissolved in the solution appropriate to processing the biological tissue. Furthermore, when the porous body without containing enzyme in pores is used, the biological tissue processing substrate can be prepared by supplying enzyme solution. Further, as for the other effect, addition of matrix necessary for mass spectroscopy and sensitizer can be added after processing the biological tissue for performing advantageous analysis.

Method for injection of enzyme in pores of the porous body which can be used may be performed by any method, for example method including spraying droplets by spray, dispenser or ink-jet. Preferable method includes ink-jet and more fine droplets can be supplied. The droplets supplying means includes continuous injection system, mechanical pressure impulse system (piezo), electrostatic suction method and film boiling system by means of electrothermal conversion (bubblejet). However, such injection method is advantageously used in case of supplying specific small region on the porous body.

Other introducing method of enzyme solution into pores includes physical method for injecting solution with stirring under the condition contacting the surface of porous with enzyme solution, electric method for introducing enzyme into pores by passing electric current to the charged support, and others, but is not limited.

If the processing method of biological tissue of the present invention is the method, for which the decomposition product of the tissue can be detected after adsorption of the decomposition product of the tissue to the support, the porous body needs not to be removed. In case that the decomposition product of the tissue is adsorbed to the porous body, the porous body needs not removed if the decomposition product of the tissue can be detected.

(Kit for Processing Biological Tissue)

A kit for processing biological tissue of the present invention is the kit for fixing proteins in the biological tissue or decomposition product of proteins, and is composed of the biological tissue processing substrate and enzyme supplying to the porous body of the substrate.

According to such composition, the substrate having contact surface with the biological tissue formed from the porous body and enzyme to be contained in the porous body in processing the biological tissue can be supplied separately, and enzyme can be supplied with more stable condition. As described above, enzyme solution can be supplied into pores of the porous body by means of ink-jet system. In the kit for processing biological tissue of the present invention, the above described support, porous body and enzyme can be used.

EXAMPLES

Example 1

In this example, a material consisting of a support with evaporated gold on a silicon wafer as the support and the porous body (pore size 3 μm) of photoresist coated material by means of photolithography is prepared and the biological tissue processing substrate containing phospholipase A2 and trypsin in pores is prepared. Proteins extracted by decomposing cell membrane lipid, and protein degradation products by degrading the proteins are adsorbed on the surface of gold. After removing photoresist material, the protein degradation products are analyzed by means of TOF-SIMS.

(1) Preparation of Porous Body

Titanium was evaporated on the silicon wafer to 5 nm, subsequently gold was evaporated to 100 nm to prepare the support. After commercially available photoresist material is coated by means of spin coat method, the photoresist material layer was patterning by photolithography to prepare the porous material having regularly pores of about 3 μm in size. The pore was passed completely from the top surface of the porous body through to the surface of the gold of the support. When the cross-sectional surface of the thus prepared porous body was observed by electron microscopy, the form as shown in FIG. 2C was observed. The surface of the substrate and the surface of pores in the photoresist porous body were prepared to hydrophilicity by UV ozone treatment.

(2) Preparation of Biological Tissue Processing Substrate

After confirming position of the porous body by using optical microscope, enzyme solution was poured into the ink-jet head reservoir, added enzyme solution dropwise into pores from the ink-jet head to fill up the inside of pores. Enzyme solution was prepared by mixing phospholipase A2 which decomposed lipid membrane of cells and trypsin which hydrolyze protein, each 10 μg/ml, and dissolved in phosphate buffer (pH 7.4). After freeze drying the enzyme solution in pores, the biological tissue processing substrate of the present invention, in which phospholipase A2 (numeral 120 in FIGS. 4A and 4B) and trypsin (numeral 122 in FIGS. 4A and 4B) were stored with powdery condition in pores 114, was prepared as shown in 4A and 4B by sublimation.

(3) Preparation of Biological Tissue Sample

Figure 7:
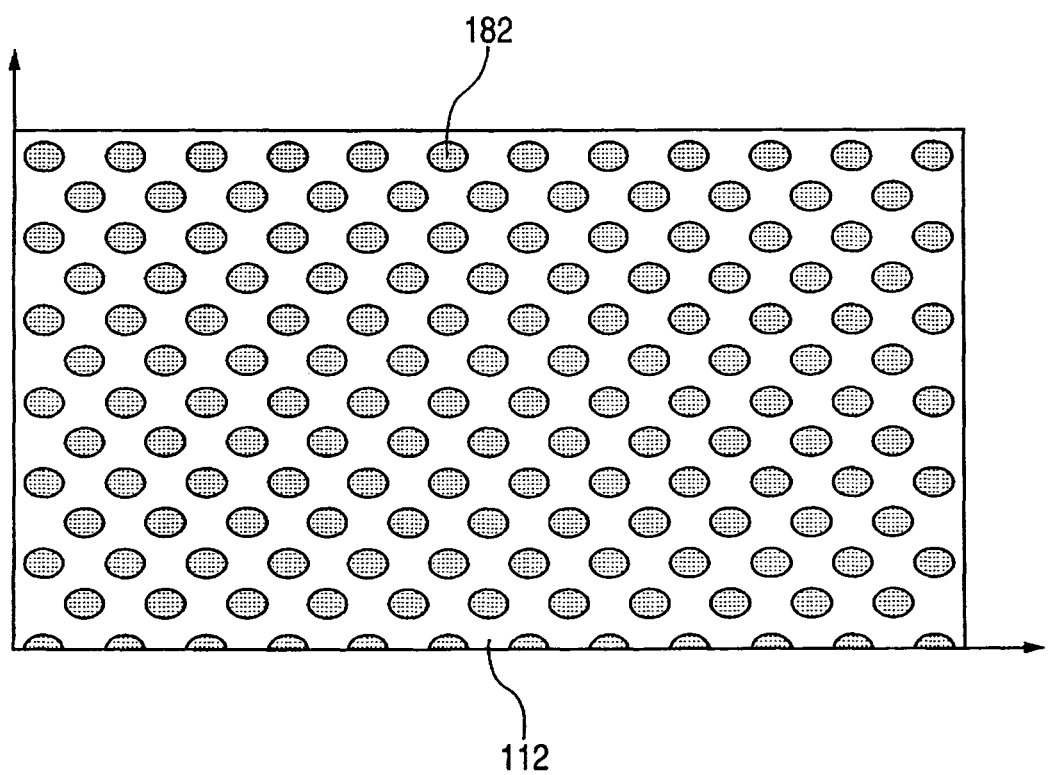
FIG. 7 shows a top view of the substrate of FIGS. 4A and 4B, which is a condition filled with a buffer, for processing the biological tissue.
Figure 8:
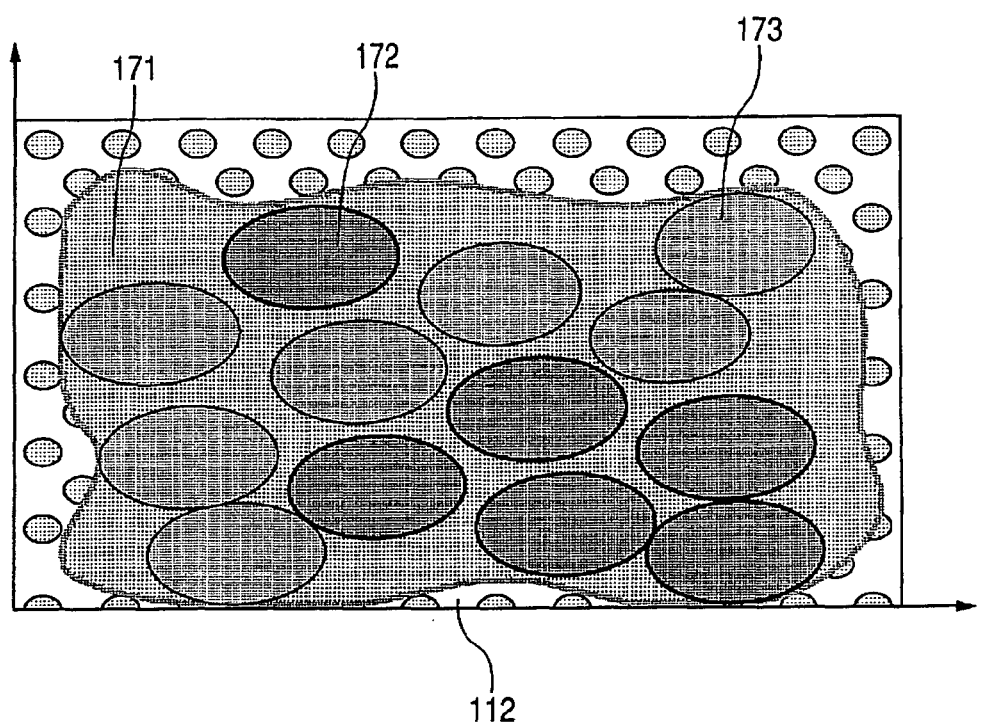
FIG. 8 shows a top view of the substrate of FIG. 7, which is a condition applied with biological tissue, for processing the biological tissue.

Phosphate buffer (pH 7.4) was poured into the ink-jet head reservoir and was added dropwise into pores of the biological tissue processing substrate as shown in 4A and 4B from the ink-jet head to fill up inside of pores as shown in FIG. 7, numeral 182. The biological tissue taken out from the living body was contacted as shown in FIG. 8 by confirming with the optical microscope. Cell membrane lipid of the biological tissue was decomposed by the action of phospholipase A2 in pores and protein extracted into pores by decomposition of cell membrane was hydrolyzed by the action of trypsin. After passing predetermined time, the biological tissue processing substrate was centrifuged under the condition with directing the support to the outer side, and the decomposition product of the protein was strongly attached to the surface of gold in the bottom of pores. After removing almost biological tissue, water content in pores was evaporated and the biological tissue processing substrate was immersed in acetone-butyl acetate to remove photoresist porous body. The substrate with almost planar surface attached with protein on the surface could be obtained.

(4) TOF-SIMS Imaging of Decomposition Product of Biological Tissue

Figure 9:
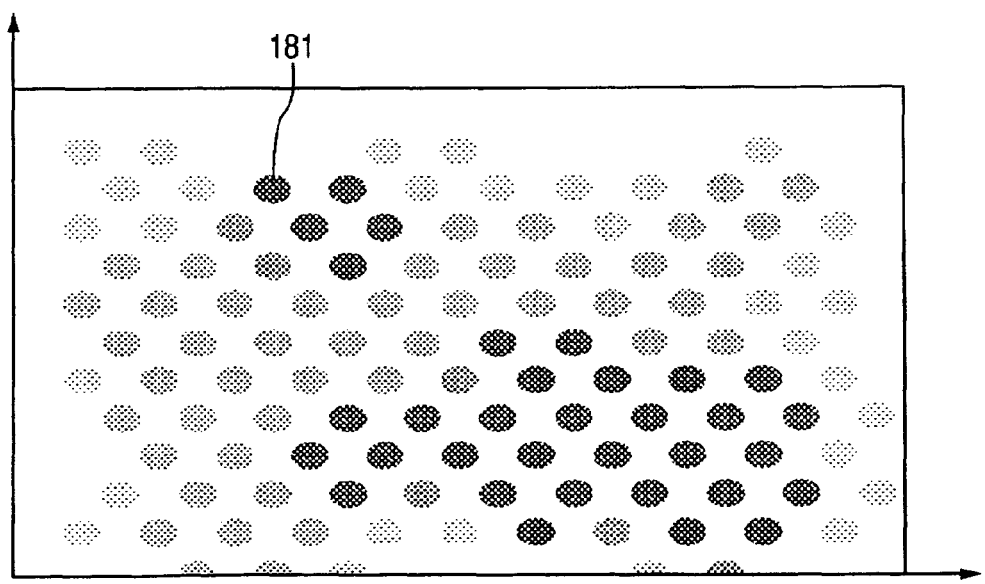
FIG. 9 shows MS imaging profile of proteins eluted from enzymatically decomposed biological tissue.

After the silicon surface of porous body was analyzed by means of TOF-SIMS under the following condition, when the decomposition product of the protein peaks were selected and subjected to imaging, signal 181 corresponding to mass peak of the protein was detected as shown in FIG. 9 on the part existing pores of the porous body in FIG. 8. In that case, characteristic peak of peptide fragment was strongly detected in position of pores existing lesioned cells, and similar peak was weakly detected in position of pores existing normal cells. As a result, when mass peak of peptide fragments was selected and subjected to imaging, the signals indicated hereinbefore were strongly detected as shown in FIG. 9 in a center on position existing lesioned cells in FIG. 8.

Results of above analysis was analyzed under the following condition by using TOF-SIMS Type IV manufactured by ION TOF after putting marks on the gold substrate. Alternatively, apparatus as shown in FIGS. 5A to 5C or FIG. 6 can be used for analysis. Measurement condition is shown below.

Primary ion: 25 kV $Ga^+$, 1.6 pA (pulse current value), random scan mode

Pulse frequency of primary ion: 7.5 kHz (150 μs/shot)

Pulse width of primary ion: about 1 ns

Diameter of primary ion beam: about 3 μm

Measurement range: 200 μm×200 μm

Number of pixels of secondary ion image: 128×128

Integrating number: 64

Secondary ion mass spectra of positive and negative were measured under the condition hereinabove. Further, the two-dimensional imaging could be obtained by reflecting the two-dimensional distribution of peptide fragments and numbers and positional interaction of lesioned cells could be identified.

Example 2

In this example, a surface of silicon wafer of the support was evaporated with gold film and the gold porous body (mean pore size 1 μm) formed by imprinting the colloidal silica arranged on a plane to the evaporated surface was used as the porous body. In two independent regions on the surface of gold, the biological tissue processing substrate containing trypsin and chymotrypsin, respectively, was prepared. The biological tissue supported by contacting previously to the transfer substrate was transferred to the biological tissue processing substrate. The degradation product of the tissue, which was extracted by hydrolyzing the cell membrane protein of the biological tissue and adsorbed in the porous body, was detected by means of TOF-SIMS (in this example no porous body was removed).

(1) Preparation of Biological Tissue Processing Substrate

Gold was evaporated at 1 μm on the silicon wafer which was cut to 1 cm square. Fine particles of silica, mean pore size 1 μm, were arranged self-assembly and subjected to pressure bonding on the cleavage fractured mica substrate. The silica fine particle surface of the mica substrate was pressed to the gold evaporated substrate to remove mica substrate. Imbedded silica particles were removed by ultrasonication in water/ethanol. The gold substrate was prepared by the above operation, and when the cross-sectional surface was observed by means of electron microscopy, the form as shown in FIG. 2H was observed. It was washed with a mixture of sulfuric acid: hydrogen peroxide=7:3 (ratio by volume). The surface of the gold substrate was observed by optical microscope and position of pores was confirmed to record the location information. On the other hand, two ink-jet cartridges were prepared. In one cartridge, a solution of 10 μm trypsin (Sigma-Aldrich, Inc.) in phosphate buffer (pH 7.4) and in the other cartridge, a solution of 10 μm chymotrypsin (Sigma-Aldrich, Inc.) in phosphate buffer (pH 7.4) were injected. Trypsin solution was supplied into each confirmed pore in the porous body region A (region of left side on the substrate in FIGS. 3A and 3B) and chymotrypsin solution was supplied into each confirmed pore in the porous body region B (region of right side on the substrate in FIGS. 3A and 3B) from head of each cartridge. By using such procedure, the substrate B for processing biological tissue having two types of enzyme region was prepared.

(2) Processing Biological Tissue

Figure 10A:
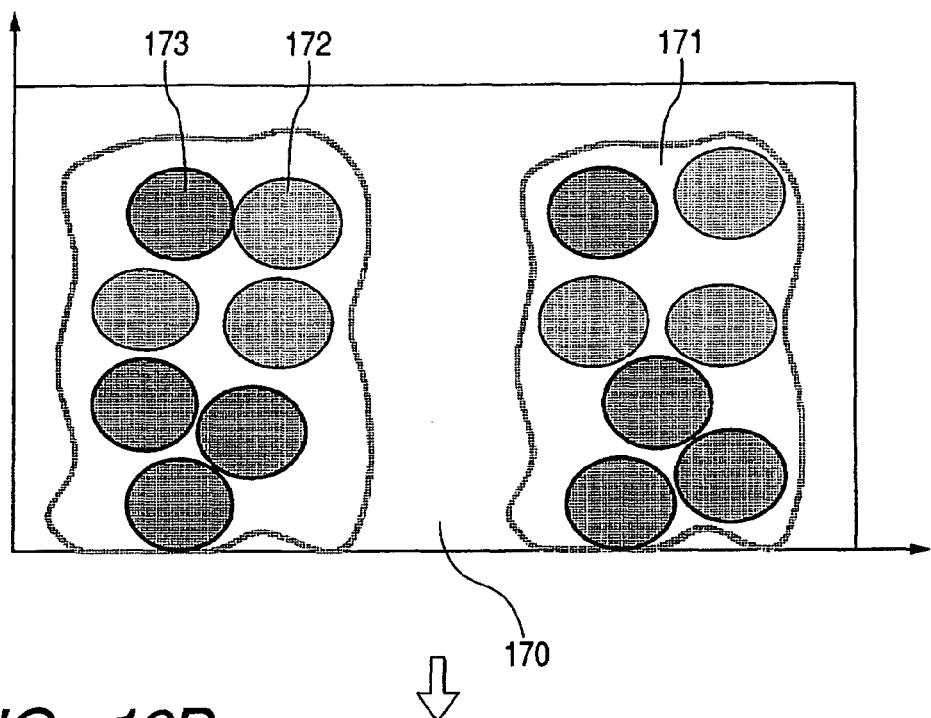
FIG. 10A shows a top view of a transfer substrate, to which the biological tissue is adhered and supported.

The biological tissue obtained from the human skin was applied once on the transfer substrate as shown in FIG. 10A and was transferred on the substrate B for processing biological tissue, and allowed to stand for 30 minutes. Membrane proteins of cells in a part of biological tissue contacted to the surface of the substrate were decomposed by the action of trypsin or chymotrypsin and peptide fragments were extracted. The peptide fragments were allowed to stand for predetermined time and the peptide fragments in pores were adsorbed on the surface of the gold porous body.

(3) TOF-SIMS Imaging of Decomposition Product of Biological Tissue

Figure 10B:
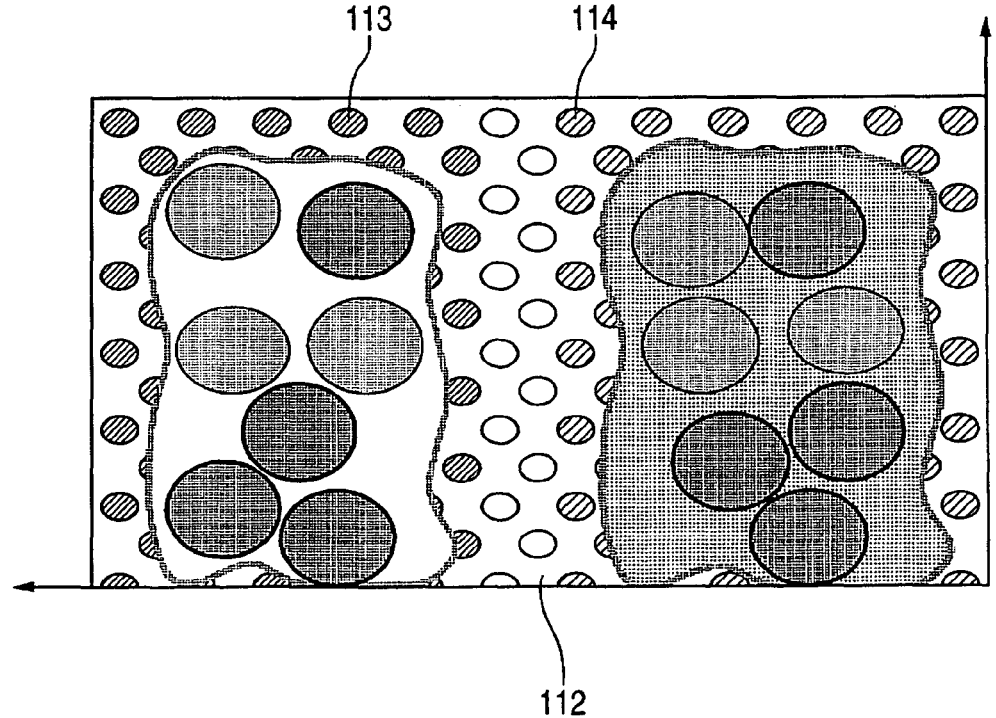
FIG. 10B shows a top view of the substrate for processing the biological tissue, to which the biological tissue supported by the transfer substrate is transferred.
Figure 11A:
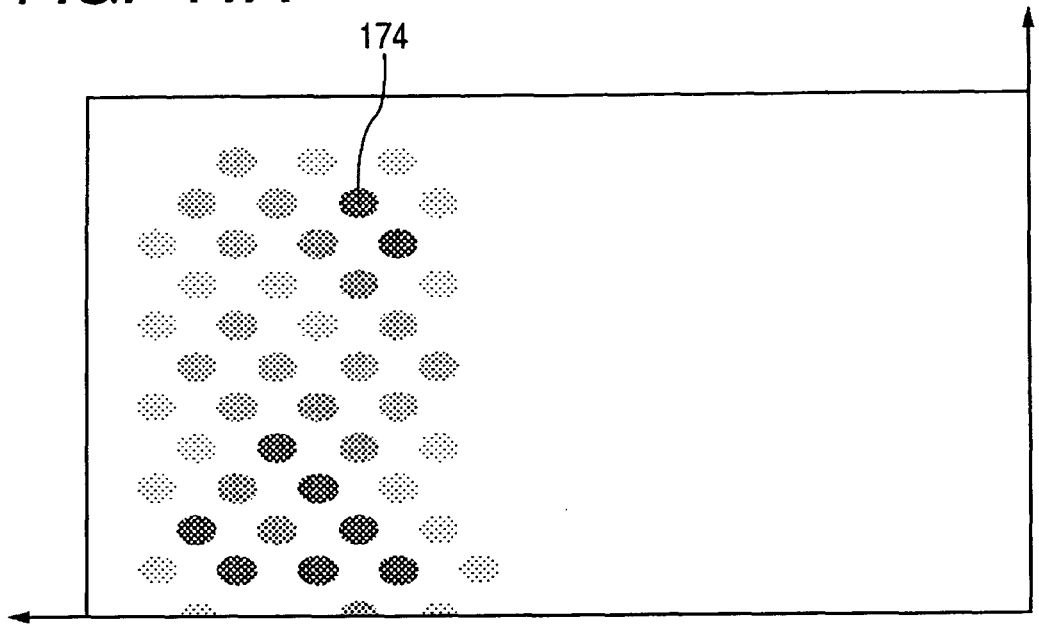
FIG. 11A shows SIMS imaging profile of the decomposition product of the tissuetissue decomposed by trypsin.
Figure 11B:
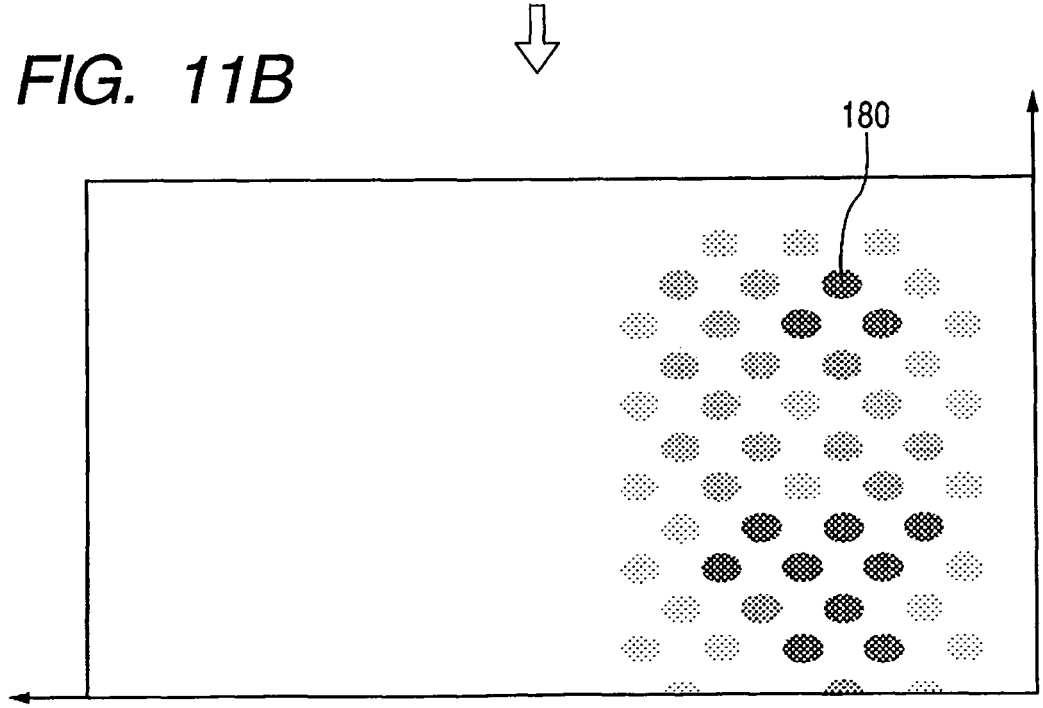
FIG. 11B shows SIMS imaging profile of the decomposition product of the tissuetissue decomposed by chymotrypsin.

After the surface of gold porous body was analyzed by means of TOF-SIMS under the following condition, when mass signal of the peptide fragments was selected and subjected to imaging, pores of the porous body were found to exist and specific peaks of peptide fragments were detected on the position existing lesioned cells. Detected peaks was different in the region of trypsin solution and that of chymotrypsin region. In the parts transferring the biological tissues shown in FIG. 10B, two mass signals hereinbefore were detected as shown in FIG. 11A and FIG. 11B. When mass signal of the decomposition product derived from some kind of proteins was selected and subjected to imaging, it was found that the signals indicated hereinbefore were detected as shown in FIG. 11A and FIG. 11B in a center on the position existing lesioned cells in FIGS. 10A and 10B.

Results of above analysis was analyzed under the following condition by using TOF-SIMS Type IV manufactured by ION TOF after putting marks on the gold substrate. Alternatively, apparatus as shown in FIGS. 5A to 5C or FIG. 6 can be used for analysis. Measurement condition is shown below.

Primary ion: 25 kV $Ga^+$, 1.6 pA (pulse current value), random scan mode
   Pulse frequency of primary ion: 7.5 kHz (150 μs/shot)
   Pulse width of primary ion: about 1 ns
   Diameter of primary ion beam: about 3 μm
   Measurement range: 200 μm×200 μm
   Number of pixels of secondary ion image: 128×128
   Integrating number: 64

Secondary ion mass spectra of positive and negative were measured under the condition hereinabove. Further, the two-dimensional imaging could be obtained by reflecting the two-dimensional distribution of peptide fragments and numbers and positional interaction of lesioned cells could be identified.

Further, in FIG. 11A and FIG. 11B, imaging profile based on individual mass peaks after performing TOF-SIMS analysis in case that same enzyme are decomposed by different enzymes are shown. In both profiles, since high signal was obtained in a center on the positions existing lesioned cells, database of proteins split by enzyme was constructed and combining pattern numbers of image profile, and as a result such database may contribute to improve reliability of biological tissue analysis.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-322311, filed Nov. 7, 2005, which is hereby incorporated by reference herein in its entirety.

What is claimed is:

1. A biological tissue processing substrate comprising:
   a planar support comprising a planar surface, at least part of the planar surface comprising a metal member disposed as a metal layer on the planar surface; and
   a porous body layer disposed on the metal layer such that a surface of the porous body layer contacts the metal layer, the porous body layer having a plurality of pores,
   wherein each of the plurality of pores extends in a vertical direction from the metal layer, and the pores extend through the porous body layer from the surface of the porous body layer contacting the metal layer to a surface of the porous body layer opposite the surface contacting the metal layer,
   wherein each of the plurality of pores comprises protease, and
   wherein the plurality of pores has a pore size ranging from 100 nm to 10 μm.

2. The biological tissue processing substrate according to claim 1, wherein each of the plurality of pores further comprises a lipid degrading enzyme.

3. The biological tissue processing substrate according to claim 1, wherein the metal member contains gold or silver.

* * * * *